United States Patent
Tu et al.

(10) Patent No.: US 6,832,111 B2
(45) Date of Patent: *Dec. 14, 2004

(54) DEVICE FOR TUMOR DIAGNOSIS AND METHODS THEREOF

(76) Inventors: Hosheng Tu, 15 Riez, Newport Coast, CA (US) 92657; Rodolfo C. Quijano, 27451 Lost Trail La., Laguna Hills, CA (US) 92653

(*) Notice: Subject to any disclaimer, the term of this patent is extended or adjusted under 35 U.S.C. 154(b) by 435 days.

This patent is subject to a terminal disclaimer.

(21) Appl. No.: 10/011,062
(22) Filed: Nov. 5, 2001

(65) Prior Publication Data
US 2003/0009110 A1 Jan. 9, 2003

Related U.S. Application Data

(63) Continuation-in-part of application No. 09/900,586, filed on Jul. 6, 2001, now Pat. No. 6,685,702.

(51) Int. Cl.$^7$ .................................................. A61B 5/05
(52) U.S. Cl. ........................................ 600/547; 600/549
(58) Field of Search ................................. 600/547, 549

(56) References Cited

U.S. PATENT DOCUMENTS

| 4,458,694 A | | 7/1984 | Sollish et al. |
|---|---|---|---|
| 4,710,550 A | | 12/1987 | Kranbuehl |
| 4,741,343 A | * | 5/1988 | Bowman et al. ............ 600/355 |
| 4,780,661 A | * | 10/1988 | Bolomey et al. ............ 324/638 |
| 5,433,717 A | * | 7/1995 | Rubinsky et al. ............ 606/20 |
| 5,630,426 A | * | 5/1997 | Eggers et al. ............... 600/547 |
| 5,807,395 A | * | 9/1998 | Mulier et al. ................. 606/41 |
| 5,810,742 A | | 9/1998 | Pearlman |
| 6,055,452 A | | 4/2000 | Pearlman |
| 6,109,270 A | | 8/2000 | Mah et al. |
| 6,176,857 B1 | * | 1/2001 | Ashley ......................... 606/32 |
| 6,241,725 B1 | | 6/2001 | Cosman |
| 6,251,073 B1 | | 6/2001 | Imran et al. |
| 6,298,726 B1 | | 10/2001 | Adachi et al. |
| 6,308,097 B1 | | 10/2001 | Pearlman |
| 6,470,217 B1 | * | 10/2002 | Fenn et al. ................. 607/101 |
| 6,640,139 B1 | * | 10/2003 | Ueberle ...................... 607/102 |

FOREIGN PATENT DOCUMENTS

| WO | WO 98/33451 | 8/1998 |
|---|---|---|
| WO | WO 01/67098 | 9/2001 |

OTHER PUBLICATIONS

Curcie DJ and Craelius W, "The Role of Thermal Feedback in Electrosurgical Tissue Heating" Technology and Health Care, vol. 3, No. 2, '95.
Pavlin CJ and Foster FS, chapter 1 in Ultrasound Biomicroscopy of the Eye, published by Springer–Verlag 1995.
Leventon W, "New Imaging Techniques Detect Diminutive Danger Signs" MD&DI pp. 48–57, Oct. 2000.

* cited by examiner

Primary Examiner—Eric F. Winakur
Assistant Examiner—Matthew J Kremer (57) ABSTRACT

A method and devices for differentiating in a given area of tissue a tumorous tissue from a normal tissue, the method comprising measuring a plurality of tissue impedance over a range of tissue temperatures and comparing the measured tissue impedance with reference tissue impedance of the normal tissue adapted for tissue differentiation. The management of tissue temperatures may be accomplished with a probe arrangement comprising two elements of different electromotive potential conductively connected at a probe junction, and passing an electrical current through the elements to reduce or raise a temperature of the probe junction in accordance with the Peltier effect.

8 Claims, 6 Drawing Sheets

DEVICE FOR TUMOR DIAGNOSIS AND METHODS THEREOF

RELATIONSHIP TO COPENDING APPLICATION

This patent application is a continuation-in-part application of application Ser. No. 09/900,586 filed Jul. 6, 2001, now U.S. Pat. No. 6,685,702 the entire contents of which are incorporated herein by reference.

FIELD OF THE INVENTION

The present invention relates generally to a medical device for diagnosing tissue and methods of use, and more particularly, to a medical device and methods for identifying abnormal tissue over a range of tissue temperatures manipulated according to the Peltier effect for effective tissue diagnosis.

BACKGROUND OF THE INVENTION

Cancer and tumor are abnormal tissue that exhibits tissue characteristics different from those of the normal tissue. Breast cancer is the leading cause of death in women. The outlook for a wonder drug or vaccine to mitigate or cure the disease at any stage is not promising. It is known that our present methods of surgery, radiotherapy, and chemotherapy are effective for long-term survival if applied when the disease is detected early and confined locally to the breast.

The latest imaging techniques may detect diminutive danger signs and help recognize disease indicators during their early stage when treatment may be most beneficial. One established technique is mammography, which is used for early detection of small, treatable breast cancers. But mammography is not infallible. According to one estimate, mammography misses 10 to 15% of all malignancies. In cases where the test results are inconclusive, patients must usually undergo biopsy procedures.

This disclosure relates to a medical device and methods of differentiating in a given area of tissue a tumorous tissue from a normal tissue by measuring tissue characteristics in situ across a range of tissue temperatures and comparing the measured tissue characteristics with reference adapted for tissue differentiation, wherein the tissue characteristics may comprise electric impedance signal, acoustic impedance signal and others.

It is known to measure the electrical impedance of tissue to determine aspects of tissue structure. A technique is available as "electrical impedance tomography" in which a number of impedance readings are taken at spaced apart locations on a region of the human body and an image derived from the data. Further, Brown et al. in PCT WO 01/67098 discloses a method of differentiating tissue types using impedance measurements over a range of frequencies. It has been shown that the tissue impedance decreases at higher frequencies, probably due to current penetration at the cell membrane.

Sollish et al. in U.S. Pat. No. 4,458,694, the disclosures of which are incorporated herein by reference, discloses systems in which the impedance between a point on the surface of the skin and some reference point on the body of a patient is determined. The reference prior art describes the use of a multi-element probe for the detection of cancer, especially breast cancer, utilizing detected variations of impedance in the breast. However, the skin surface impedance measurement is not site-specific for breast cancer diagnosis.

Pearlman in U.S. Pat. Nos. 5,810,742, 6,055,452, 6,308, 097 and "New Imaging Techniques Detect Diminutive Danger Signs" by W. Leventon (MD&DI pp 48–57, October 2000), the disclosures of which are incorporated herein by reference, describe transspectral impedance scanning (T-scan) systems as a new mammography for cancer identification. The T-scan measures the movement of electricity through tissue because cancers have impedance values that are much lower than those of noncancerous tissue. It is further disclosed that the capacitance and conductance of malignant tissue are about 50 times greater than that of either normal tissue or benign lesions. However, the T-scan neither measures the site-specific minute tumor or cancer in vivo, nor manipulates the tested tissue at a range of temperatures suitable for enhancedly differentiating the impedance signal of the cancers from that of noncancerous tissue over a range of tissue temperatures.

The sonography uses high frequency sound waves to perform a wide variety of diagnostic examinations. The ultrasound frequencies typically range from about 20 kHz to above 100 MHz. The principles of diagnostic sonography rest in the tissue attenuation, reflectivity, transmission or scattering, which has been described elsewhere (C J Pavlin and F S Foster, Ultrasound Biomicroscopy of the Eye, Chapter 1, by Springer-Verlag 1995).

Adachi et al. in U.S. Pat. No. 6,298,726, the entire contents of which are incorporated herein by reference, discloses an acoustic impedance measuring apparatus that emits ultrasonic waves to a target object and measures the acoustic impedance of the target object by ultrasonic waves fed back. The reference fails to teach manipulating the target tissue object at a range of temperatures to enhancedly differentiate the acoustic impedance signal of the cancer tissue object from that of noncancerous tissue object.

It would overcome the afore-mentioned disadvantages by providing a needle probe and a method of differentiating in a given area of tissue a tumorous tissue from a normal tissue, the method comprising measuring tissue impedance, electrically, acoustically or thermally, across a range of tissue temperatures and comparing the measured tissue impedance with reference tissue impedance of the normal tissue adapted for enhanced tissue differentiation.

To maintain the tissue temperature over a range, say from 20° C. to 45° C., thermal energy and cryogenic cooling is provided alternatively. Conventionally thermal energy could be clinically applied to the tissue by radiofrequency heating, while the cryogenic cooling could be provided by a circulating cooled medium in the probe. A radiofrequency probe with a liquid-cooled electrode is conventionally used to manipulate the tissue temperature over a range of clinical interest. However, such a device is bulky and also cumbersome to handle the liquid cooling system. In one embodiment, the range of tissue temperatures of the present invention is about 20° C. to 45° C. that is suitable and compatible with the body tissue.

U.S. Pat. No. 5,348,554 to Imran et al. discloses a catheter system with a cooled electrode. Specifically, an electrode having a chamber therein is provided with a circulated cooling liquid to cool the electrode. U.S. Pat. No. 6,241,666 to Pomeranz et al., and U.S. Pat. No. 6,015,407 to Rieb et al. also disclose a catheter system with a modified cooled electrode, mostly with a liquid coolant arrangement that is bulky, expensive or poses unnecessary risk to a patient. The entire contents of the above-cited patents are incorporated herein by reference.

A radiofrequency catheter with a liquid-cooled electrode includes extra auxiliary equipments, such as a circulating pump, a cooling liquid source, control instruments, and accessories. As disclosed in U.S. Pat. No. 5,348,554, the cooled liquid is intended to cool the inner chamber of the tip electrode. However, the temperature of the outer surface of the electrode may rise to an unacceptable level resulting in tissue degradation, blood clot, or coagulation. As is well known to an ordinary technician skilled in the art that the resistive heat of radiofrequency ablation comes from the tissue-electrode contact surface. Even with a liquid-cooled setup thereof, the electrode temperature might be far above the cell necrosis temperature.

A probe for quantifying the impedance over a range of tissue temperature would be ideal for breast cancer diagnosis. Johnson et al. in U.S. Pat. No. 4,860,744 discloses a thermoelectrically controlled heat medical catheter, which is incorporated herein by reference. More particularly, Johnson et al. discloses a system and methods for providing controlled heating or cooling of a small region of body tissue to effectuate the removal of tumors and deposits, such as atheromatous plaque. Though Johnson et al. teaches a medical catheter in accordance with the Peltier effect adapted for thermoelectric heating/cooling for destruction of diseased tissue and/or tumors in various parts of the body, Johnson et al. does not disclose a method for manipulating the tissue temperatures so as to enhancedly differentiate the impedance signal of the cancers from that of noncancerous tissue over a range of tissue temperatures.

Larsen et al. in U.S. Pat. Nos. 5,529,067, 5,755,663, and 5,967,976 disclose methods and apparatus for use in procedures related to the electrophysiology of the heart, such as identifying or evaluating the electrical activity of the heart, diagnosing and/or treating conditions associated with the electrophysiology of the heart, entire contents of which are incorporated herein by reference. Specifically, Larsen et al. teaches an apparatus having thermocouple elements of different electromotive potential conductively connected at a junction and reducing the temperature of the junction in accordance with the Peltier effect for cooling the contacted heart tissue. However, Larsen et al. does not teach a method for diagnosing a target tissue comprising providing thermal or cryogenic energy to the target tissue and simultaneously or subsequently measuring tissue impedance over a range of tissue temperatures.

It is one object of the present invention to provide a method of differentiating a tumorous breast tissue from a normal tissue, wherein the method comprises measuring tissue characteristics across a range of tissue temperatures and comparing the measured tissue characteristics with reference characteristics of the normal tissue. There is a clinical need to screen the patients by a less invasive needle probe technique so as to lower the number of unnecessary biopsies performed each year.

SUMMARY OF THE INVENTION

In general, it is an object of the present invention to provide a device and a method for diagnosing and/or treating a target tissue using a medical device that is suitable for the intended applications in treating tumorous tissue, comprising a catheter, a probe, a cannula, an endoscopic instrument, a lapascopic instrument or the like.

It is another object of the present invention to provide a method of differentiating in a given area of tissue a tumorous tissue from a normal tissue, the method comprising measuring a plurality of tissue impedance over a range of tissue temperatures and comparing the measured tissue impedance with reference tissue impedance of the normal tissue adapted for tissue differentiation.

In one embodiment, the method of manipulating the tissue temperatures over the range of interest may be provided by a probe junction, the probe junction being conductively connected to two elements of different electromotive potential and electrical current being passed through the elements to reduce/raise temperature of the probe junction in accordance with the Peltier effect.

In another embodiment, the target tissue may be selected from a group consisting of tumor, cancerous tissue, arrhythmia, pulmonary vein, benign prostate hyperplasia, breast tumor, breast cancer, inflammation, atherosclerosis, vulnerable plaque, or the like. The therapeutic thermal energy may be selected from a group consisting of radiofrequency energy, microwave energy, laser energy, infrared energy, ultrasound energy, and combination thereof.

It is another object of the present invention to provide an electric impedance, acoustic impedance, or biochemical impedance over a range of tissue temperatures for tissue differentiation.

It is still another object of the present invention to provide a probe for treating tissue subsequent to identifying a tumorous tissue. The treatment methods may comprise thermal ablation, cryogenic ablation, delivering a therapeutic means for treating the tumorous tissue at about said given area of tissue, wherein the therapeutic means is selected from a group consisting of drug, chemotherapy, radiation, and combination thereof.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

It is one object of the present invention to provide a method for enhancedly differentiating in a given area of tissue a tumorous tissue from a normal tissue. The method comprises measuring a plurality of tissue impedance values over a range of tissue temperatures and comparing the measured tissue impedance values with reference tissue impedance value of the normal tissue adapted for tissue differentiation with high specificity and high sensitivity so as to reduce the numbers of unnecessary biopsy or surgery. The impedance measurement of the present invention may comprise tissue electrical impedance, tissue acoustic impedance, tissue biochemical impedance, and the like.

For background illustration and information, each breast has about 15 to 20 overlapping sections called lobes. Within each lobe are many smaller lobules, which end in dozens of tiny bulbs that can produce milk. The lobes, lobules and bulbs are all linked by thin tubes called ducts, whereby the ducts lead to the nipple in the center of a dark area of skin called the areola. Fat fills the spaces around the lobules and ducts. There are no muscles in the breast.

Each breast also contains blood vessels and lymph vessels. The most common type of breast cancer begins in the lining of the ducts and is called ductal carcinoma. Another type, called lobular carcinoma, arises in the lobules. When breast cancer is found and treated early, the chances for survival are better. A screening mammogram is the best first-step tool available for finding breast cancer early, before symptoms appear. A mammogram is a special kind of x-ray used for checking breast changes in women who have no signs of breast cancer. Although mammograms are the best way to find breast cancer early, they do have some limitations. A mammogram may miss some cancers that are present (false negative) or may find things that turn out not to be cancer (false positive).

Other types of non-invasive breast examinations may include ultrasonography, transspectral impedance scanning or palpation. However, an abnormal area detected by a non-invasive breast screening may cause concern and require further evaluation, typically done by either surgical biopsy or needle biopsy. Although more than a million biopsies are performed each year, only about 15 to 20% of them detect the presence of cancer. This means that the vast majority of biopsies would not need to be performed if an effective screening method could be made available.

Certain electrical properties of tumor cells differ from those of the normal tissues that surround them. Tumor cells demonstrate greater permittivity and conductivity of electrical current. It is disclosed and generally agreed that cancers have impedance values much lower than those of noncancerous tissue and can be identified by the manner in which they influence the electrical current path. Other tissue properties between normal tissue and tumorous tissue are also parameters for tissue differentiation, particularly over a physiological range of tissue temperatures that are compatible with tissue.

The term "tissue characteristics" herein is intended to mean any or a combination thereof of the following properties: tissue electrical properties (such as electrical impedance, electrical conductance, electrical capacitance, dielectric constants, and the like), biochemical properties (such as oxygen level, pH level, electrolytes concentration, temperature, and the like), structural properties (such as ultrasound signal, acoustic impedance, electromagnetic potential, light transmission, and the like), and physical properties (such as lump, fat tissue density, appearance, and the like). It is one object of the present invention to differentiate the tissue characteristics by a needle probe operated over a range of tissue temperatures that are compatible with tissue. In one embodiment, the range of controlled tissue temperatures of the present invention is about 20° C. to 45° C. that is suitable and compatible with the body tissue. In another preferred embodiment, the range of controlled tissue temperatures could be from about 20° C. to about 38° C. or from 38° C. to about 45° C.

Curcie and associates reports a study on the role of thermal feedback in electrosurgical tissue heating (Curcie D J et al., *Technology and Health Care*, vol. 3, no. 2, 1995). In the study, a bioheat equation was applied to a resistive model of tissue that showed tissue impedance decreasing with heating in a simulation model. It is further suggested by Curcie et al. from the dynamic interaction study between output power and tissue impedance that the impedance of living tissue generally declines with increasing temperature, a behavior opposite to that of most materials. It is disclosed hereby that the impedance difference between normal tissue and tumorous tissue is enhanced for differentiable tissue diagnosis at a tissue temperature away from the normal body temperature.

It has been found that fatty tissue exhibits significantly different dielectric constant and conductivity than muscle tissue. Since most cancer develops in post-menopausal women (assumed in the age 50 and up group), and since the post-menopausal breast is characterized by a proliferation of adipose (fatty) tissue, it is conceivable to detect cancer in the post-menopausal breast by in situ measurement of the appropriate electrical properties. It is assumed, therefore, that the problem of detecting a tumor in the breast reduces to that of detecting a small region characterized by certain electrical characteristics embedded in a larger region of different electrical characteristics (essentially, those of fat).

A medical probe for in vivo diagnosis and/or therapy has been disclosed in U.S. Pat. No. 6,241,725 to Cosman and U.S. Pat. No. 6,109,270 to Mah et al., the disclosures of which are incorporated herein by reference. In one particular embodiment, Cosman teaches percutaneously inserting a radiofrequency probe into the tumor and raising the temperature for direct thermal destruction after imaging the tumor by various imaging modalities. As one example, stereotactic methods may be used to locate, calculate, and guide the ablation probes into the region of the tumor, such as real-time CT and MRI imaging. Further, real-time evaluation of the procedures can be carried out using an ultrasonic detector in conjugation and proximity to the radiofrequency electrode.

Referring to FIGS. 1 to 6, what is shown is an embodiment of a medical device or probe having site-specific diagnostic and/or therapeutic capabilities comprising measuring the tissue characteristics, particularly the impedance characteristics, of the target tissue region over a range of tissue temperatures, wherein the tissue temperature is manipulated and controlled by the probe during the diagnosis phase. In a preferred embodiment, the tissue temperature is manipulated by the Peltier effect mechanism associated with a Peltier effect probe junction mounted onto the medical probe. In one preferred embodiment, the Peltier effect probe junction comprises the impedance-measuring element.

Figure 1:
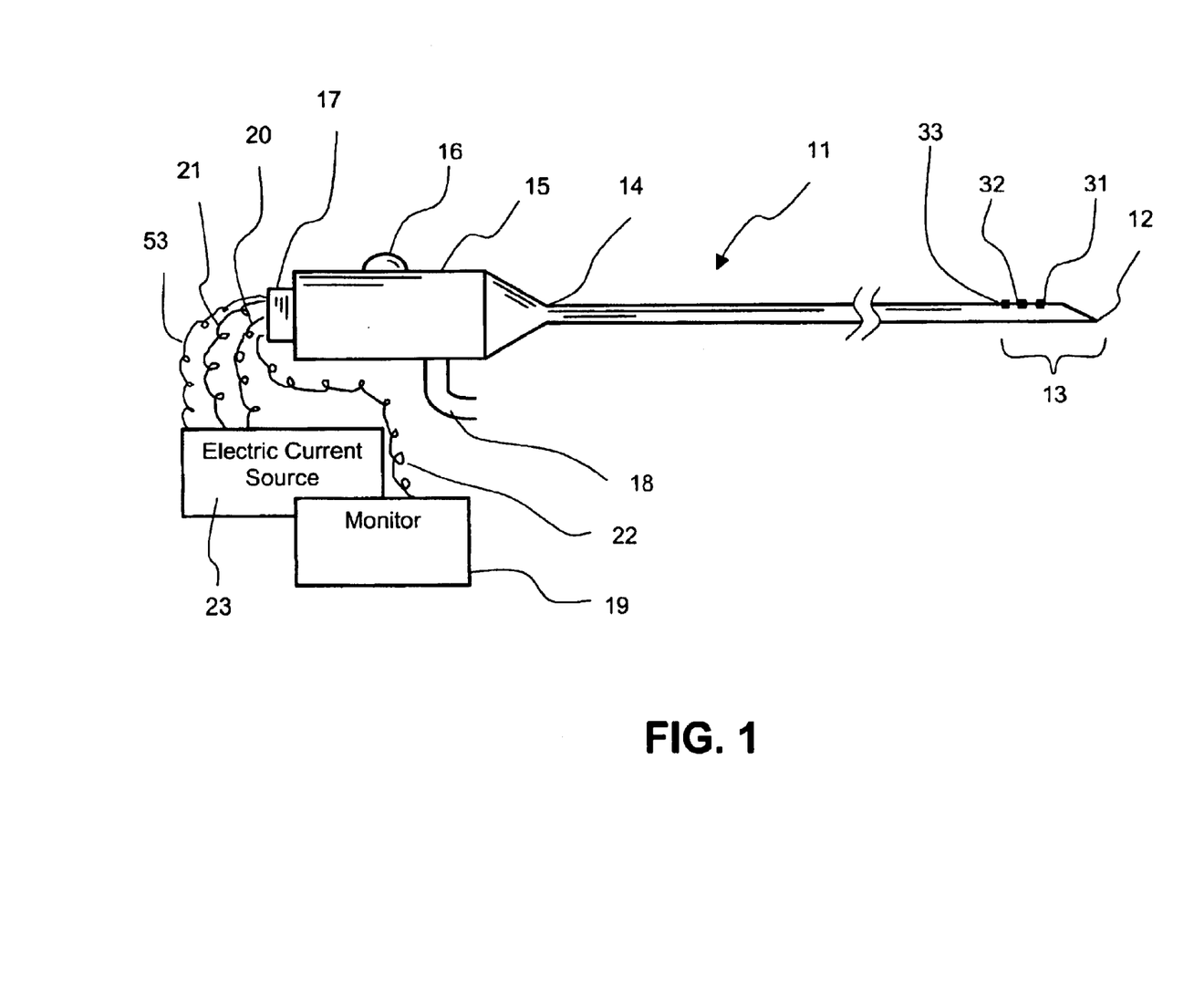
FIG. 1 is an overall view of a medical device constructed in accordance with the principles of the present invention.

FIG. 1 shows an overall view of a medical device constructed in accordance with the principles of the present invention. The medical device of the present invention may comprise a catheter, a probe, a cannula, an endoscopic instrument, a lapascopic instrument or the like that is suitable for the intended applications in differentiating and treating tumorous tissue. By "tumorous tissue" is meant herein for any abnormal tissue including tumor, cancerous tissue, arrhythmia, pulmonary vein, benign prostate hyperplasia, breast tumor, breast cancer, inflammation, atherosclerosis, vulnerable plaque, or the like inside the body of a patient. It is one object of the present invention to provide a method of differentiating in a given area of tissue an abnormal or tumorous tissue from a normal tissue, the method comprising measuring a plurality of tissue impedance readings over a range of tissue temperatures and comparing the measured tissue impedance readings with reference tissue impedance of the acceptable representative normal tissue adapted for qualitative and/or quantitative tissue differentiation.

In one embodiment, the medical probe 11 comprises a flexible or rigid probe body having a distal end 12, a proximal end 14, at least a lumen therebetween, and a distal section 13. A handpiece 15 is attached to the proximal end 14 of the probe body. The probe may be provided at its proximal end a connector 17 to an external electric current source 23 having a plurality of insulated conducting wire sets 20, 21 for providing current to an metallic element assembly (heating or cooling) comprising a plurality of impedance measuring elements 31, 32, 33 at the probe distal section 13. The impedance measuring transmission arrangement 22 is provided from the connector 17 to the monitor setup 19. The electric current source 23 may be a high frequency current source or other energy source, for example radiofrequency energy, ultrasound energy, infrared energy, laser energy, microwave energy, or the like.

The distal section 13 and the distal end 12 of the probe 11 may be configured for easy insertion into a tissue of a patient with a small incision. The sharpness of the distal end 12 is suitable for insertion and the probe body is generally smooth with optional hydrophilic surface coating. The probe can be a cylindrical, oval or other suitable configuration with optional side or end openings. The outer diameter of the probe is preferable less than 5 mm, more preferably 2 mm or smaller. The probe can be several inches or longer suitable for intended applications. To enhance the tissue contact with the impedance measuring elements, the section of the probe containing the impedance measuring elements 31, 32, 33 may be constructed bulged outwardly.

The probe handpiece 15 may also comprise at least a switch control arrangement 16 provided to control the electrical current, the current flow direction, impedance measurement, temperature sensing, and other operating conditions. In a preferred embodiment, the electrical conductor arrangement 53 is to provide an electrical current to the impedance-measuring element 31, 32, 33 or equivalent for a monopolar-mode or bipolar-mode impedance measurement. In operation, when the impedance measuring elements contact a tissue, the first tissue impedance between the elements 31 and 32 can be measured. Similarly, the second tissue impedance between the elements 32 and 33 can be measured. In this illustrated case, the first tissue impedance might indicate an abnormal tissue while the second tissue impedance might indicate a normal tissue or vice versa. The probe of the present invention may further comprise at least three spaced apart micro-electrode elements for measuring tissue impedance, the measured tissue impedance from a first and a second of the at least three micro-electrode elements being compared to the measured tissue impedance from the second and a third of the at least three micro-electrode elements for tissue differentiation.

Because cancers have impedance values substantially lower than benign or normal tissue, they can be identified by their effects in altering the electrical current path. Typically a low voltage of about 1.0 volt is applied directly to the patient through the medical probe. The frequencies can vary or pre-programmed between 50 Hz to about 50 kHz or higher. There are three basic methods for measurement of electric impedance: bridge, voltage and current method. The last one can be applied in two variations on electrodes number: bipolar and tetrapolar. In impedance spectrometry a generator with changeable frequency from few Hz to kHz or MHz is used. The tetrapolar current method is the best for measuring of tissue impedance because of its independence from electrode-skin impedance variability and homogeneous distribution of current density. To mitigate the influence of artifacts on measuring results, the impedance spectrometry may have a special arrangement with fast result analysis for detection and automatic elimination of artifacts by repetition of measurement. In practice, a small constant current, typically 800 $\mu$Amp at a fixed frequency, usually 50 kHz, is passed between electrodes through the tissue and the voltage drop between electrodes provides a measure of impedance.

The measured impedance data is fed to an external monitor 19, which may be connected to the electric current source 23 for feedback or closed-loop current control. For "monitor" is meant herein an instrument that can store, analyze, compare, and report data, wherein the monitor has a computer software comparing real-time measurements to a set of archived parameters that indicate the presence or absence of cancer. The results as displayed on the monitor instantly should help doctors make the right diagnosis early and develop a treatment plan for the patient. The probe may further comprise an optional attachment 18 configured and adapted for delivering therapeutic means for treating the tumorous tissue at about the target area of tissue, wherein the target area of tissue may comprise breast tissue, prostate tissue, brain tissue, or the like as defined in the term "tumorous tissue" of the present invention. Further, the therapeutic means of the present invention may be selected from a group consisting of drug, chemotherapy, radiation, and combination thereof, which are all well known means for cancer treatment.

Tumor is an abnormal mass of tissue that results from excessive cell division. Tumor performs no useful body function and could be either benign or malignant. Cancer is a disease in which abnormal cells divide without control; cancer cells can invade nearby tissues and can spread through the bloodstream or lymphatic system to other parts of the body. One characteristic for cancer is its ample supply of blood through abnormally large numbers of capillaries. Therefore, it is conceivable that at an elevated tissue temperature, the lowering of the impedance for normal tissue may be faster than that of tumorous tissue due to warm-blood effect. In another statement, it is also conceivable that the increase of the impedance for normal tissue at a lowered tissue temperature may be faster than that of tumorous tissue due to warm-blood effect.

Figure 2:
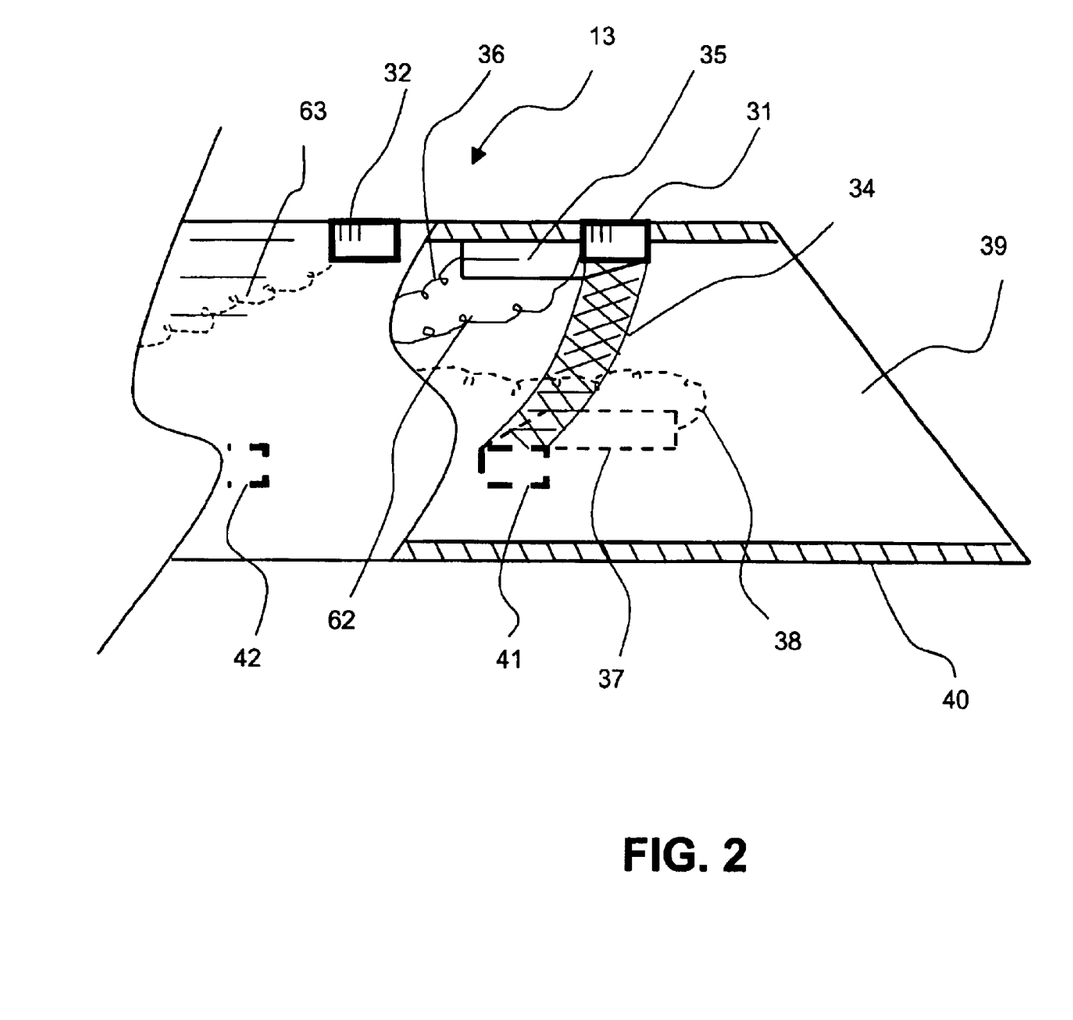
FIG. 2 is a cross-sectional view of the tip section assembly of the medical device, showing impedance measuring elements and two elements of different electromotive potential conductively connected at a probe junction.

FIG. 2 shows a cross-sectional view of the tip section assembly 13 of the medical probe 11, showing impedance measuring elements 31, 32 and elements 35, 37 of different electromotive potential conductively connected at a probe junction 34. The "probe junction" of the present invention is intended to mean a junction with a somewhat curved configuration to provide cryogenic energy or thermal energy around or surround the metallic element assembly or equivalent adapted for adjusting the temperature of impedance measuring element 31, 32 over a range of temperatures. In an alternate embodiment the probe junction of the present invention may serve as the tissue measuring element or the therapeutic energy-treating element. Further, the probe junction may be selected from a group consisting of circular, semi-circular, ring, rounded, oval, random curved shape or other suitable configuration. In an alternate embodiment, an opening 39 at the distal end 12 of the medical probe 11 is configured and adapted for delivering therapeutic means for treating the tumorous tissue in situ.

Figure 4:
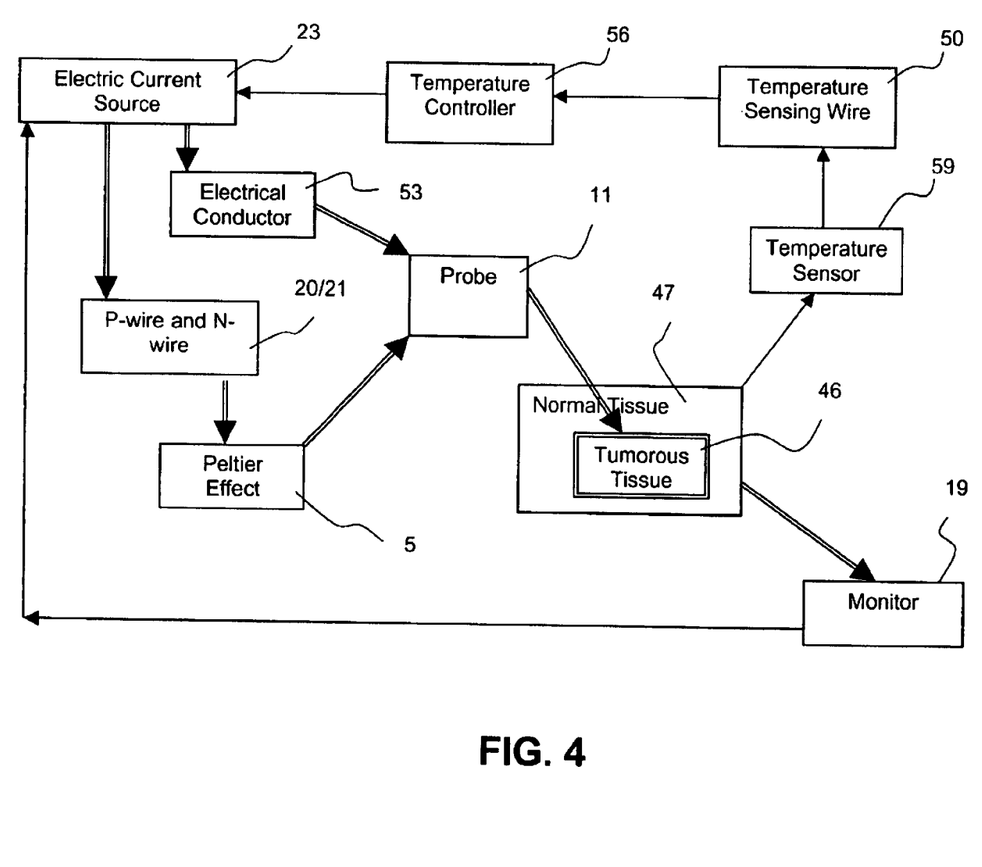
FIG. 4 is a schematic illustration of the principles of the medical probe for tumor diagnosis.

According to the principles of the present invention as illustrated in FIG. 4, the medical probe 11 may optionally comprise a temperature sensor 59 secured at about the tissue measuring elements 31, 32 for monitoring the tissue temperature, wherein the measured temperature is relayed through a temperature sensing wire 50 to a monitor or to a temperature controller 56 for controlling the thermal/cryogenic energy supply, when needed.

Figure 3:
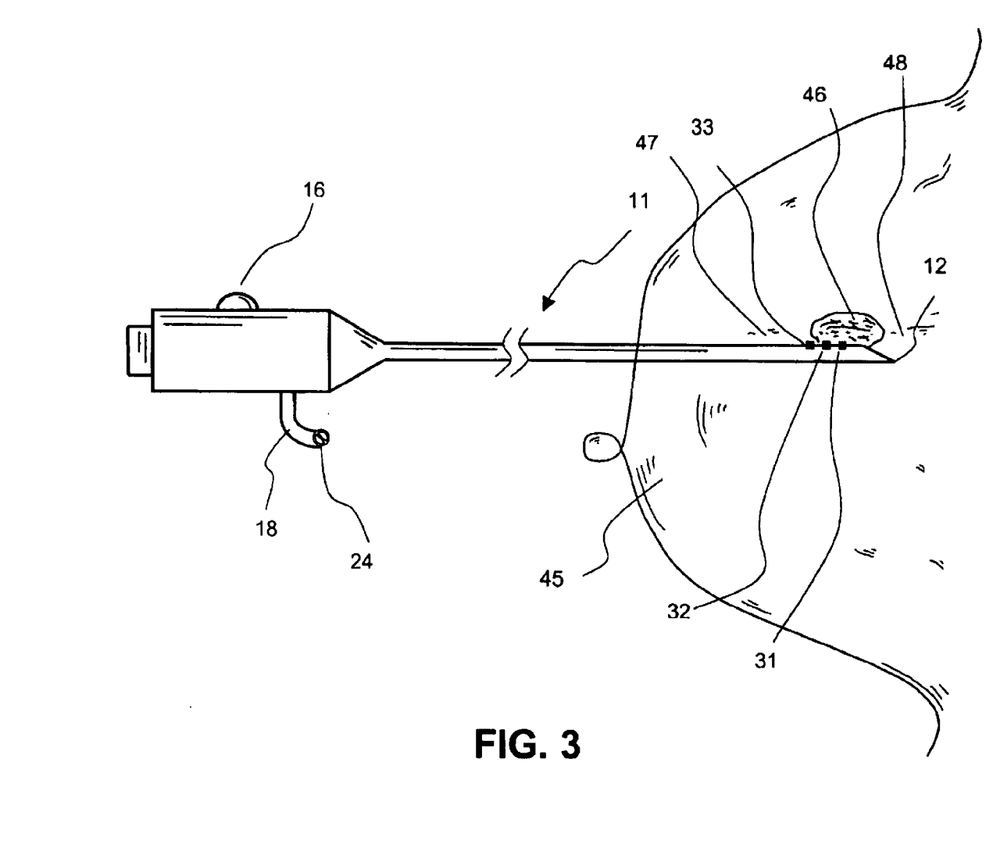
FIG. 3 is a simulated view of the medical probe inserted into a breast for tissue differentiation.
Figure 6:
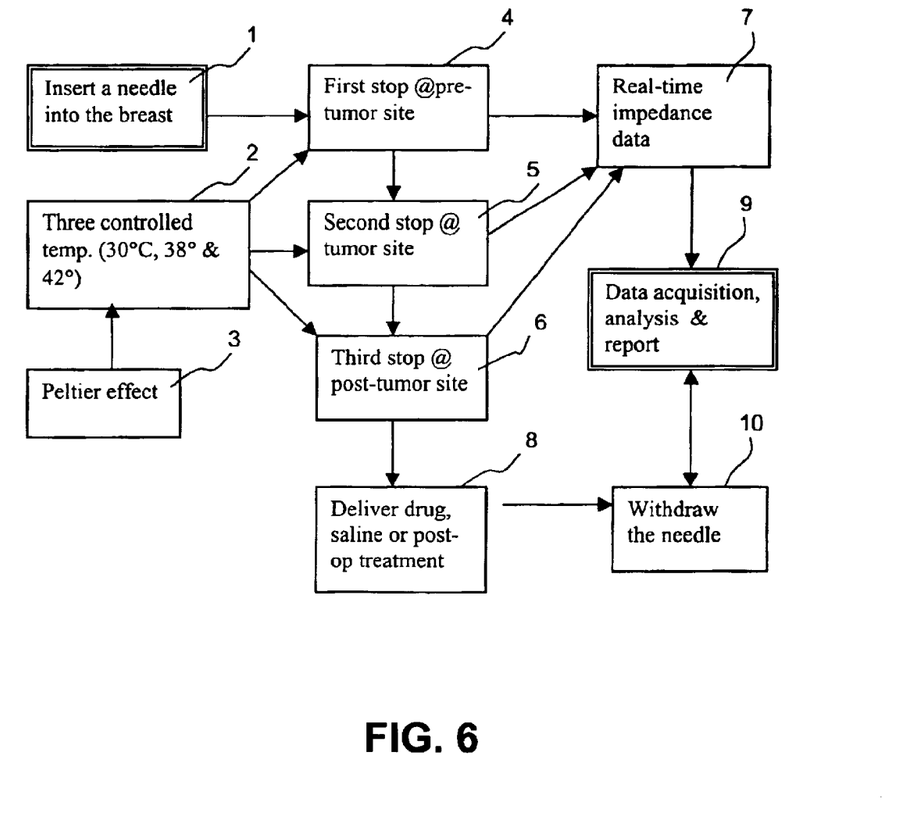
FIG. 6 is a schematic diagram illustrating the methods for operating a medical probe according to the principles of the present invention.

FIG. 3 shows a simulated view of the medical probe inserted into a breast for tissue differentiation while FIG. 6 shows a schematic diagram illustrating the methods for operating a medical probe according to the principles of the present invention. For illustration purposes, a medical probe 11 is inserted (step 1) into the breast 45 of a patient approaching the target tissue zone 46. The probe passes and briefly stops (step 4) at a pre-tumor site 47 for measuring the impedance characteristics (step 7) over a range of tissue temperatures. The tissue temperature is manipulated (step 2) by the Peltier effect mechanism (step 3) built-in with the probe; for example a tissue temperature of 30° C., normal body temperature of 38° C., tissue temperature of 42° C. or others. The mode of operating heating and cooling of the present invention according to the Peltier effect may be a simultaneous, an alternate, a sequential, other pre-programmed, or combination thereof mode.

As the medical probe 11 advances further (step 5) into the tumorous tissue zone 46, the impedance tissue readings (step 7) at certain tissue temperatures (step 2) are taken either continuously or discretely. To obtain further reference readings from normal tissue, the medical probe 11 may stop (step 6) briefly at a post-tumor site 48. All data are fed (step 9) to the monitor 19 for data acquisition, analysis and report. In an alternate embodiment, the medical probe 11 may be configured for delivering drug, saline or other post-treatment therapy (step 8). The probe comprises delivering a therapeutic means for treating the tumorous tissue at about the target tumorous tissue, wherein the therapeutic means is selected from a group consisting of drug, chemotherapy, radiation, and combination thereof. The therapeutic means may further comprise a step of providing thermal energy, cryogenic energy or combination thereof, to treat the tumorous tissue. The activating mechanism 24 for triggering the therapeutic means is mounted at about the attachment 18 of the probe 11.

Blewett et al. in U.S. Pat. No. 6,106,521 discloses an apparatus with a needle-like probe for thermal treatment of tissue. Behl in U.S. Pat. No. 6,212,433 discloses a system for treating a target tissue beneath a tissue surface by deploying a needle-like electrode array. Durgin, Jr. et al. in U.S. Pat. No. 5,522,815 discloses an integrated catheter with a needle for diverse in situ tissue therapy. Mulier et al. in U.S. Pat. No. 6,238,393 discloses an apparatus for creating a bi-polar virtual electrode through a needle-like inner electrode. The contents of all the above-cited patents are incorporated herein by reference. A needle or needle-like electrode for penetrating into a tissue is well known to one ordinary artisan skilled in the art of electrode ablation.

As described in U.S. Pat. Nos. 4,860,744, 5,529,067 and generally shown in FIG. 5 of the present invention, general principles of the Peltier effect are illustrated below as an example. The therapeutic element 81 utilizes one pair of P (positive) and N (negative) thermoelectric elements or legs. The materials of the thermoelectric therapeutic element 81 may be configured in a variety of different ways such as bar or wire forms design. The P leg 82 and N leg 83 are electrically separated along their lengths, but are conductively joined at one end. The contact junctions 86, 87 represent one of junctions. With reference to U.S. Pat. No. 4,860,744, a molybdenum silicide plate to join the two legs at the contact junctions 86, 87 may be optionally used. The molybdenum silicide plate, as one example, that connects the legs at the contact junction 86, 87 is referred to as a cool junction "shoe" 80 (can be a hot junction shoe if the current is reversed). The P and N legs are separately connected at a second end to connector wires 84, 85. The ends of the thermoelectric elements are referred as junctions. The other set of junctions are the reference junctions 89, 90. The manner in which P and N legs are formed and the Peltier effects is known to those skilled in the art and forms no part of the present invention.

Figure 5:
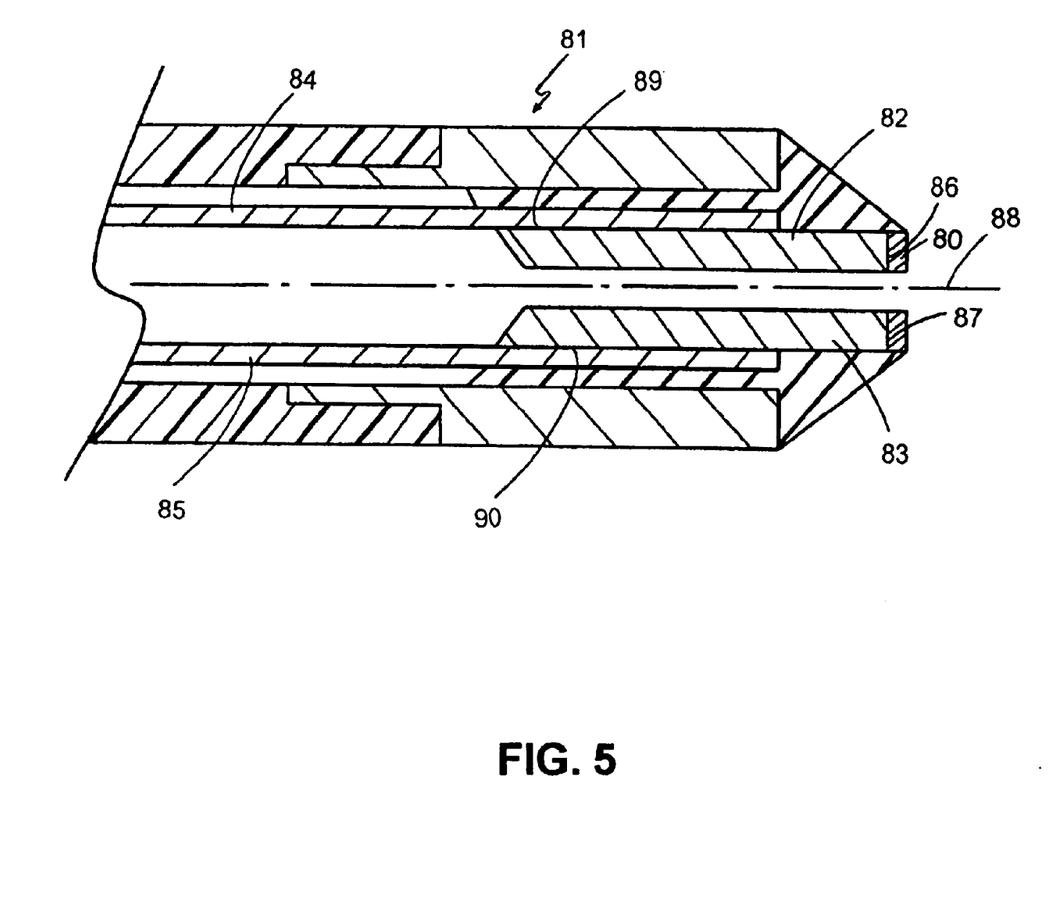
FIG. 5 is a longitudinal cross-sectional view of the distal end portion of a representative device utilizing the Peltier effect as an example.

Referring to FIG. 5, thermoelectric cooling of the contact junctions 86, 87 occurs when an electrical current is passed through the legs in the N to P direction, which is controlled by the power switch control 16 at the handpiece 15. The reference junctions 89, 90 experience heating when this electrical current is passed through the legs. Additional Joulean heating occurs in the legs 82, 83 because of the internal electrical resistance of the legs. This Joulean heating diminishes the cooling of the cold junction shoe 80. There is a need to disperse the heat generated at the legs and at the reference junctions 89, 90. The reference junction is illustratively represented with elements 41, 42 in FIG. 2.

As shown in FIG. 2, the electromotive elements 35 and 37 for the probe junction 34 are configured and arranged so that the reference junctions 41, or 42 are adjacent a surface of the probe body 40. By such an arrangement, the heat generated at the reference junctions does not interfere with the tissue temperature of interest. Therefore, the probe junction 31 or 32 can maintain its coolness (or heat) effective for measuring the tissue impedance over a range of tissue temperatures. In a certain embodiment, the probe junction 31 may preferably be configured permeably porous for fluid or small particles, such as electrolytes, to flow through. The flow-through fluid may stabilize the impedance readings with little noise. In another embodiment, the probe junction is impermeable to any fluid or particles.

The acoustic impedance is a property of tissues that depends on the speed of sound and the tissue's density. Acoustic impedance is important because it is involved with reflection and production of echoes from tissues. The term "acoustic impedance" as used herein is not ultrasound attenuation. The acoustic impedance is found by multiplying a tissue's speed of sound times its density. In general, impedances of soft tissues differ from one another by only a small amount. As an ultrasound pulse propagates through tissue, any interface formed by two tissues that have different acoustic impedances will cause some of the sound energy to be reflected. The difference in acoustic impedances between the normal tissue and the tumorous tissue is crucial in determining the amount of sound reflected versus the amount transmitted at the interface, wherein the difference in acoustic impedances is a tissue characteristic that is used for tissue differentiation of the present invention. It is further disclosed that the difference in acoustic impedances between the normal and the tumorous tissues is amplified or diminished over a range of tissue temperatures. The difference in acoustic impedances over a range of tissue temperatures is used for tissue differentiation of the present invention.

The term "biochemical tissue impedance" is meant to indicate herein the impedance (also known as resistance to measuring techniques in this embodiment) relating to the biochemical properties of tissue for tissue differentiation between normal tissue and tumorous tissue. The biochemical tissue impedance may comprise oxygen level, pH level, temperature due to inflammation, and the like. A microprobe element for measuring partial pressure of oxygen can be mounted at the probe tip section 13 that can aid in detection of hypoxia, an indication of tumor malignancy. An ion-selective micro-electrode element for measuring the tissue pH and a thermometer element for measuring the tissue temperature can also be mounted at the probe tip section 13 adapted for the intended diagnosis of biochemical tissue impedance over a range of tissue temperatures that is manipulated and controlled through the medical probe pf the present invention.

From the foregoing description, it should now be appreciated that a medical device and methods comprising incorporating a method of differentiating in a given area of tissue a tumorous tissue from a normal tissue, the method comprising measuring a plurality of tissue impedance over a range of tissue temperatures and comparing the measured tissue impedance with reference tissue impedance of the normal tissue adapted for enhanced tissue differentiation has been disclosed. While the invention has been described with reference to a specific embodiment, the description is illustrative of the invention and is not to be construed as limiting the invention. Various modifications and applications may occur to those who are skilled in the art, without departing from the true spirit and scope of the provisional application.

What is claimed is:

1. A method of differentiating in a given area of tissue a tumorous tissue from a normal tissue, the method comprising measuring a plurality of tissue impedances over a range of tissue temperatures and comparing said measured tissue impedances with reference tissue impedances of the normal tissue adapted for tissue differentiation, wherein said measured tissue impedances are acoustic tissue impedances.

2. The method of claim 1, further comprising delivering a therapeutic means for treating the tumorous tissue at about said given area of tissue.

3. The method of claim 2, wherein the therapeutic means is selected from a group consisting of drug, chemotherapy, radiation, and combination thereof.

4. The method of claim 1, further comprising a step of providing thermal energy to treat the tumorous tissue.

5. The method of claim 4, wherein the thermal energy is selected from a from a group consisting of radiofrequency energy, ultrasound energy, infrared energy, microwave energy, and laser energy.

6. The method of claim 1, further comprising a step of providing cryogenic energy to treat the tumorous tissue.

7. A method of differentiating in a given area of tissue a tumorous tissue from a normal tissue, the method comprising: measuring a plurality of tissue impedances over a range of tissue temperatures and comparing said measured tissue impedances with reference tissue impedances of the normal tissue adapted for tissue differentiation; and inserting a probe at about said given area of tissue, wherein said probe is configured to comprise a Peltier effect for achieving said range of tissue temperatures, wherein said probe further comprises at least three spaced apart micro-electrode elements for measuring tissue impedance, the measured tissue impedance from a first and a second of the at least three micro-electrode elements being compared to the measured tissue impedance from the second and a third of the at least three micro-electrode elements for tissue differentiation.

8. The method of claim 7 further comprising a step of providing thermal energy to treat the tumorous tissue, wherein the thermal energy is selected from a group consisting of radiofrequency energy, ultrasound energy, infrared energy, microwave energy, and laser energy.

* * * * *